United States Patent [19]

Stewart et al.

[11] 4,409,246

[45] Oct. 11, 1983

[54] YEAST STRAIN FOR FERMENTING HIGH PLATO VALUE WORTS

[75] Inventors: Graham G. Stewart; Thomas E. Goring; Ingeborg Russell, all of London, Canada

[73] Assignee: Labatt Brewing Company Limited, London, Canada

[21] Appl. No.: 285,854

[22] Filed: Jul. 22, 1981

[51] Int. Cl.³ .................... C12C 11/04; C12N 1/18
[52] U.S. Cl. .................... 426/16; 426/29; 426/62; 435/256
[58] Field of Search .............. 426/11, 16, 60, 62, 426/29; 435/245, 255, 256

[56] References Cited

U.S. PATENT DOCUMENTS 4,140,799  2/1979  Nagodawithana et al. ...... 426/16 X
4,318,929  3/1982  Clement et al. ................ 435/256 X

FOREIGN PATENT DOCUMENTS 880875   9/1971  Canada.
1597724  8/1970  France ........................ 426/16
730804   4/1980  U.S.S.R. ...................... 426/16

OTHER PUBLICATIONS

Rose, A. H., Economic Microbiology, vol. 1, Alcoholic Beverages, Academic Press, N. Y., 1977 (pp. 81–96 & 123).
Chemical Abstracts, vol. 90: 150251(e)–150253(g), 1979, (p. 458).
Haraldson et al., Yeast Strains For Concentrated Substrates, Eur. J. Appl. Microbiol. Biotechnol., vol. 13, Sep. 1981, (pp. 34–38).
DeClerck, J. De., A Textbook of Brewing, vol. 1, Chapman & Hall, Ltd., London, 1957, (pp. 388–397).

*Primary Examiner*—David M. Naff
*Attorney, Agent, or Firm*—Fisher, Christen & Sabol

[57] ABSTRACT

The specification discloses a novel brewers' yeast strain and a method of manufacturing the same. The yeast is a strain of *Saccharomyces cerevisiae* and has been deposited at the National Collection of Yeast Cultures, Norwich, England under the number 962. Morphologically the giant colony of the novel strain can be described as a circular colony having a slightly serrated periphery, a convex surface topography with a central, globular dome and exhibiting primary concentric convolutions and secondary radial convolutions which, in combination, impart a rough appearance to the surface. The novel ale strain has the advantages that it is effective in worts having high plato values and is a bottom-cropping strain.

9 Claims, 11 Drawing Figures

YEAST STRAIN FOR FERMENTING HIGH PLATO VALUE WORTS

This invention relates to a novel yeast strain suitable for use in the brewing of beer and to a method of preparing the same.

In the brewing of beer, i.e. ale and lager, ale yeast strains (*Saccharomyces cerevisiae*) are traditionally top-cropping strains and lager yeast strains (*Saccharomyces uvarum (carlsbergensis)*) are bottom-cropping strains. That is, when the attenuation of the wort, which may be broadly defined as the conversion of fermentable substrate to alcohol, has attained a certain level, the discrete yeast cells of most ale strains adhere or aggregate to an extent that, adsorbed to bubbles of carbon dioxide, they will rise to the surface under quiescent conditions (e.g. when the medium is not agitated) where they are "cropped" by being skimmed off. In the case of lager strains, the aggregated cells are not adsorbed to bubbles of carbon dioxide and settle out of suspension to the bottom of the vessel where they are "cropped" by various standard methods.

One of the limitations of the known ale yeast strains is that they do not function satisfactorily in worts having plato values (°P) higher than about 14.5°P and values of only about 9°P to 12°P are usually required. The plato value (°P) is defined as the weight of dissolved solids, expressed as a percentage, in water at 15.6° C. Generally, the higher the plato value at which a yeast strain will function, the greater is the conversion of fermentable substrate to alcohol for a given volume of wort. Consequently, the resultant fermentation product would be one of higher than usually desired final alcohol content and would generally be diluted before packaging. Since the dilution to obtain a standard, commercially acceptable product would occur at the end of the brewing process, the overall throughput of such a brewery system would be substantially increased over a conventional system. Furthermore, beers produced from such high plato worts generally exhibit improved colloidal haze and flavour stability.

In view of the economic advantages possible in fermenting worts of higher plato values, there has been a substantial amount of research carried out in the hope of obtaining a yeast strain which will function at such higher plato values in the range of about 16°P to 18°P, i.e. a yeast strain which will remain in the body of the wort until substantial or total conversion of the fermentable sugars to alcohol at the higher plato values has occurred. As an alternative, attempts have been made to maintain known yeast strains in the body of the wort by mechanical means, such as continuous stirring, in the hope that the yeast would continue to function if maintained in contact with the wort. However, this has proved to be inefficient and in many cases more expensive because of the extra energy required to operate such mechanical means. Furthermore, many such attempts have been frustrated by difficulties of product flavour match with present commercially acceptable standards.

The inventors of this invention have now discovered a yeast strain which is an ale yeast (species *Saccharomyces cerevisiae*) that not only functions at high plato values, e.g. up to about 18°P, but also flocculates to the bottom of the fermenting vessel when conversion or attenuation has been substantially completed (the latter feature, as noted above, is usually characteristic of a lager strain rather than an ale strain).

The present novel organism was found to be a component of a mixture of ale yeasts maintained by the assignee. The organism was isolated and biologically pure cultures thereof were produced by techniques considered standard by those skilled in the art and can be obtained upon request from the permanent collection of the National Collection of Yeast Cultures (termed "NCYC" herein), Food Research Institute, Norwich, Norfolk, England. The accession number of the organism in this repository is NCYC No. 962.

Thus, according to one aspect of the present invention, there is provided a novel brewers' yeast strain of *Saccharomyces cerevisiae* having NCYC No. 962.

In another aspect, the invention provides a method of manufacturing a novel brewers' yeast strain which comprises propagating in a suitable standard nutrient medium with oxygenation (either in pure or diluted form, such as air) a *Saccharomyces cerevisiae* brewers' yeast strain NCYC No. 962.

In a further aspect, the invention provides a brewing process wherein a malt wort is prepared; supplemented, where desired, with an adjunct; fermented with brewers' yeast; and, following completion of the fermentation, finished to the desired alcoholic brewery beverage; the improvement comprising, fermenting said wort with *Saccharomyces cerevisiae* brewers' yeast strain NCYC No. 962.

The advantage of the yeast strain of the present invention (referred to herein as strain 962 for the sake of convenience) is that it has both bottom-cropping characteristics as well as the ability to ferment high specific gravity worts. The bottom-cropping characteristic is advantageous because of increased utilization in the brewing industry of large conical-based vessels for fermenting the wort, and bottom-cropping is especially facile in such vessels. Thus, strain 962 is particularly well adapted for use with continuous brewing techniques as well as batch-wise brewing.

The fact that strain 962 can ferment worts having high plato values is economically advantageous in that use of such worts allows dilution with water at a much later stage in the processing, generally prior to packaging. By reducing the amount of water required in the majority of process stages, increasing production demands can be met without the expansion of existing brewing, fermenting and storage facilities and the overall throughput of an existing brewery system can be substantially increased by the use of strain 962. Consequently, the brewing process can be carried out at a reduced overall cost, including a reduced energy cost.

Thus, while a number of bottom-cropping ale strains are known, the dual characteristics of bottom-cropping and the ability to ferment high gravity worts makes strain 962 of the present invention especially useful in the brewing of ale.

The specific morphological and physiological characteristics of strain 962 are set out below. It should be noted, however, that the strain is definitely an ale strain rather than a lager strain according to classical yeast taxonomy in that it cannot completely ferment the trisaccharide raffinose (fructose-glucose-galactose) because the organism lacks the requisite enzyme, melibiase (as described by J. Lodder, in "The Yeasts"; North-Holland: Amsterdam [1970]). This is also confirmed by the fact that the beer produced by strain 962 is considered by taste panelists to be an ale which compares most favourably to the presently available popular commercial ales.

In the following discussion, reference is made to the accompanying drawings, in which.

MORPHOLOGICAL AND PHYSIOLOGICAL CHARACTERISTICS OF NOVEL YEAST STRAIN 962

I. PHYSICAL CHARACTERISTICS—giant colony morphology

The giant colony morphology of the organism was determined according to the method described by M. Richards in Journal of The Institute of Brewing, Volume 73; pages 162-166 (1967).

The procedure outlined by Richards was strictly adhered to with the following exceptions:
(a) Preparation of the medium:
  (i) in the preparation of the plates, biphenyl was not added to the melted medium (usually included as a fungicide) as this compound was found to inhibit growth of the organism to some extent; and
  (ii) as the source of this organism was not a commercial one and all culturing procedures were carried out under aseptic conditions, there was no real danger of bacterial contamination of the medium and the addition of aureomycin (bacteriocide) was, therefore, not necessary.
(b) Production of giant colonies:
  (i) the incubation of the plates was four weeks at a temperature of about 21° C.

Figure 1A:
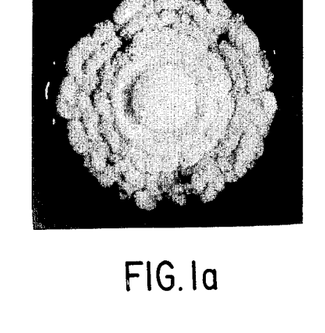
FIG. 1(a) is a photograph at 6X magnification of a giant colony of the novel strain of the present invention.

As illustrated in FIG. 1(a), morphologically the giant colony of the novel strain may be described as being a circular colony having a slightly serrated periphery, a convex surface topography with a central, globular dome. Furthermore, the surface topography consistently exhibits primary concentric convolutions and secondary radial convolutions which, in combination, impart a rough appearance to the surface. In colour, the colony appears matte cream to light beige.

Figure 1B:
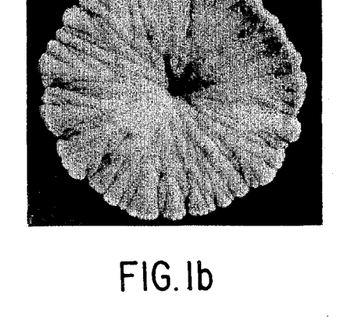
FIGS. 1(b) and 1(c) are photographs at 6X magnification of the giant colonies of two known ale strains.
Figure 1C:
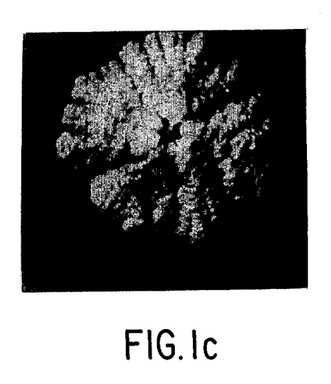
Figure 1D:
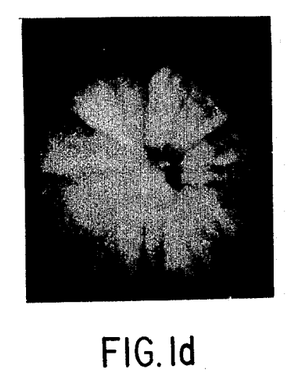
FIG. 1(d) is a photograph at 6X magnification of the giant colony of a known lager strain.

FIGS. 1(b), 1(c) and 1(d) are three additional photographs of two other ale strains and one lager strain of genus Saccharomyces for comparison. FIGS. 1(b) and 1(c) show the giant colonies of the ale strains and FIG. 1(d) illustrates that of the lager strain at a magnification of about 6X.

Single colonies of strain 962 may be subcultured using standard slant culturing techniques. A medium found very satisfactory for this type of culture was a malt-yeast extract-glucose-peptone (MYGP) medium prepared according to the method described by L. J. Wickerham, in Technical Bulletin No. 1029 (1951), U.S. Department of Agriculture. The incubation temperature and period were as described hereinbefore for the production of giant colonies. Single colonies so produced were stored at about 4° C. Long term maintenance of subcultures is carried out satisfactorily by conventional techniques, such as storing the so-produced organisms under liquid nitrogen or lyophilizing the organisms and storing same at room temperature.

II. PHYSIOLOGICAL CHARACTERISTICS

A number of experiments were carried out to determine the comparative effect of such parameters as wort gravity, etc. on the flocculation of selected representative strains of Saccharomyces. There are a number of definitions of yeast flocculation but that generally preferred states that "flocculation" is the phenomenon wherein yeast cells adhere in clumps or aggregates and separate rapidly from the medium in which they are suspended.

The causative factor governing this phenomenon exhibited by certain strains has not been settled definitely but is held by many to be controlled by a fine balance between the role played by the genetic make-up of a particular strain, the cell surface structure and the environmental conditions.

The flocculation characteristics of a particular strain of Saccharomyces are one of its most important properties when considering the selection of a strain for brewing purposes. An important aspect of the flocculation characteristic of a brewing strain is the period during the fermentation cycle that the yeast flocculates. One of the most troublesome problems encountered is premature flocculation of the yeast which results, inter alia, in incomplete attenuation of the wort, i.e. incomplete conversion of the fermentable substrate into ethanol. On the other hand, while it may be desirable for a certain quantity of yeast to remain in suspension for purposes of secondary fermentation, it is also possible that yeast may flocculate insufficiently, thus making its removal from the fermented wort, in order to produce a bright beer, troublesome and economically unattractive, for example, problems with filtration may result. Moreover, insufficient flocculation may lead to "off-flavours" due to autolysis of the excessive quantity of suspended yeast. Ideally, the yeast would not flocculate significantly until maximum attenuation of the wort has occurred. It is with the above concept in mind, that flocculation was chosen as a primary parameter to be examined in these comparative studies.

Flocculence was measured under conditions very similar to the static (no agitation) fermentation encountered in brewing. The yeast was precultured at about 21° C. in a hopped wort containing about 30% corn adjunct, prepared by general procedure well known to those skilled in the art, and then inoculated into about 16 liters of identical wort in a 20 liter unstirred glass fermenter, unless otherwise stated. An inoculation level of about 0.25% wet weight of cells (about $1.35 \times 10^7$ viable cells/milliliter) was used in all experiments together with an incubation temperature of about 21° C. unless stated otherwise. Sequential wort samples were taken throughout the course of the fermentation and the specific gravity and concentration of yeast in suspension determined, by standard methods, on each sample.

The fermentability of the wort with each yeast under study was determined by incubating about 200 ml of wort with approximately 4 grams of the yeast strain in a 300 ml flask on a New Brunswick Gyrotory Shaker at about 160 r.p.m. at approximately 21° C. for about 72 hours. Unless otherwise stated 11.8°P hopped wort was used (about 30% corn adjunct). The difference between the original gravity and the gravity after shaker fermentation represents 100% attenuation (fermentability) for the wort and yeast strain in question.

(a) Effect of Wort Gravity on Yeast Flocculation

As stated hereinbefore, experimental conditions were adhered to which resembled as closely as possible the commercial, static fermentation environment in that the yeast was precultured in wort and then inoculated into approximately 16 liters of hopped wort at about 21° C. in a 20 liter unstirred glass fermenter. The results are shown graphically in FIG. 2, wherein the concentration of yeast in suspension is plotted against the percentage attenuation of the wort.

Figure 2:
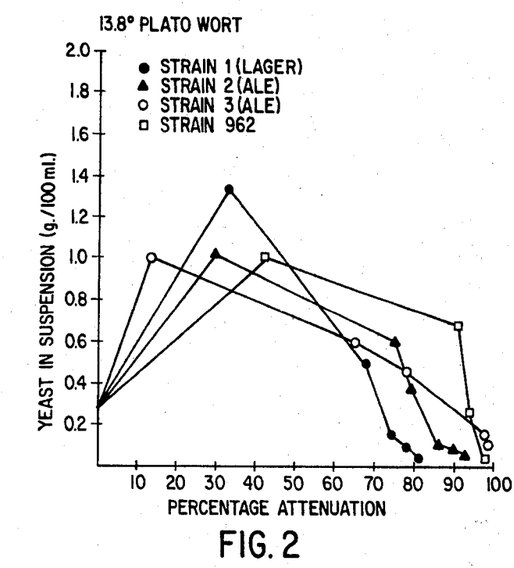
FIG. 2 is a graph showing the flocculation characteristics of several strains of brewers' yeast, including the novel strain of the invention in a 13.8°P wort.

In FIG. 2, strain 1 is a lager strain while strains 2 and 3 are top-cropping ale strains. The yeast strain of the present invention, as noted above, is designated as strain 962. All of the other strains are maintained in the culture collection of the assignee and have been ascribed arbitrary identification numbers for the purpose of this specification.

From FIG. 2, it may be noted that ale strains 3 and 962 were able to ferment the wort substantially completely leaving little yeast in suspension at the end of fermentation.

It is noteworthy that the yeast strain of the present invention did not flocculate to any significant extent until the wort had been almost completely attenuated at which point flocculating occurred at a very rapid rate. Among the advantages realized by the rapid rate of flocculation are that the occurrence of off-flavours due to yeast autolysis is minimized and the removal of the yeast from the fermented wort is obviously facilitated. Additionally, FIG. 2 illustrates the versatility of the present strain in that it functions very well in even the normal range of wort specific gravity. The ale strain 2 fermented the wort to about 93% attenuation whereas the lager strain 1 fermented the wort to about 81%. The under attenuation exhibited by strains 1 and 2 were the apparent result of premature flocculation of the yeast. FIG. 2 shows that even in a 13.8°P wort some of the yeast strains are induced to flocculate too soon leaving a significant quantity of unfermented extract.

Figure 3:
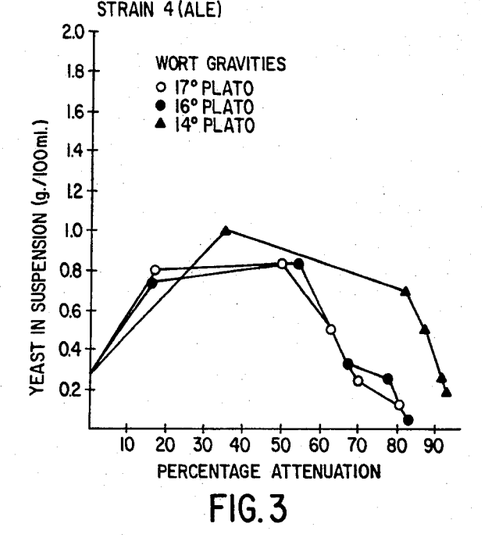
FIG. 3 is a graph showing the effect of wort gravity on the flocculation characteristics of a known ale yeast strain.
Figure 4:
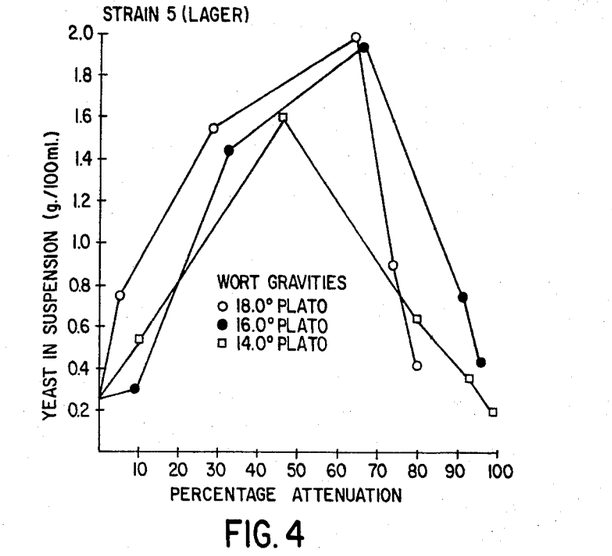
FIG. 4 is a graph showing the effect of wort gravity on the flocculation characteristics of a known lager yeast strain.
Figure 5:
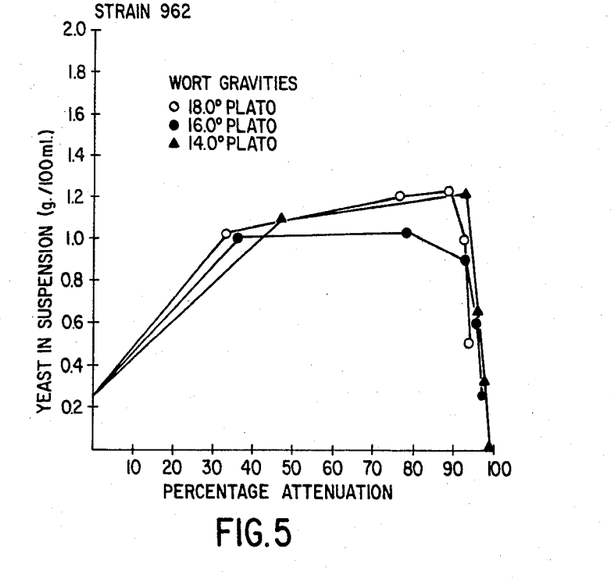
FIG. 5 is a graph showing the effect of wort gravity on the flocculation characteristics of the novel yeast strain of this invention.

The effects of higher gravity worts were studied in some detail by utilizing worts with gravities ranging from about 12°P to 18°P. The flocculation characteristics of three strains of yeast are shown in FIGS. 3 to 5, in which, as in the case of FIG. 2, the concentration of yeast in suspension is plotted against the percentage attenuation of each wort. FIG. 3 shows that although strain 4 satisfactorily fermented out a 14°P wort, fermentation in 16°P and 17°P worts resulted in premature flocculation and only approximately 80% of the fermentable extract was attenuated. This strain illustrates the general trend exhibited by many ale yeast strains and some, although less frequently, lager strains.

While in the case of both lager strain 5 (FIG. 4) and ale strain 962 (FIG. 5) increasing wort gravity generally resulted in greater quantities of yeast remaining in suspension, the lager strain 5 was unable to completely ferment out the high gravity wort. That is, at 18°P, the concentration of yeast strain 5 in the suspension was about 0.4% (w/v) with a final attenuation of only about 80% whereas the same gravity wort fermented by strain 962 provided values of about 0.5% and 95%, respectively. Additionally, approximately half the yeast population of strain 5 had flocculated out at about 73% attenuation of the 18°P wort. The data shown in FIGS. 3 to 5 also suggest that in high gravity worts a greater proportion of the total yeast population becomes non-flocculant and remains in suspension concomittant with an apparent loss of its ability to ferment wort sugars. Presumably it is the ability to ferment maltotriose that is decreased since, as is well documented in the literature, unfermented maltotriose is invariably present in "sticking" or "hanging" fermentations. The reason(s) for this observation is not clear and is, in any case, not essential to the understanding of the present invention. However, the amount of increased yeast remaining in suspension in higher gravity worts as shown in FIGS. 3 to 5 can be removed by standard methods of extracting yeast, e.g. by centrifugation.

(b) Effect of Growth Temperature on the Flocculation Characteristics

Figure 6:
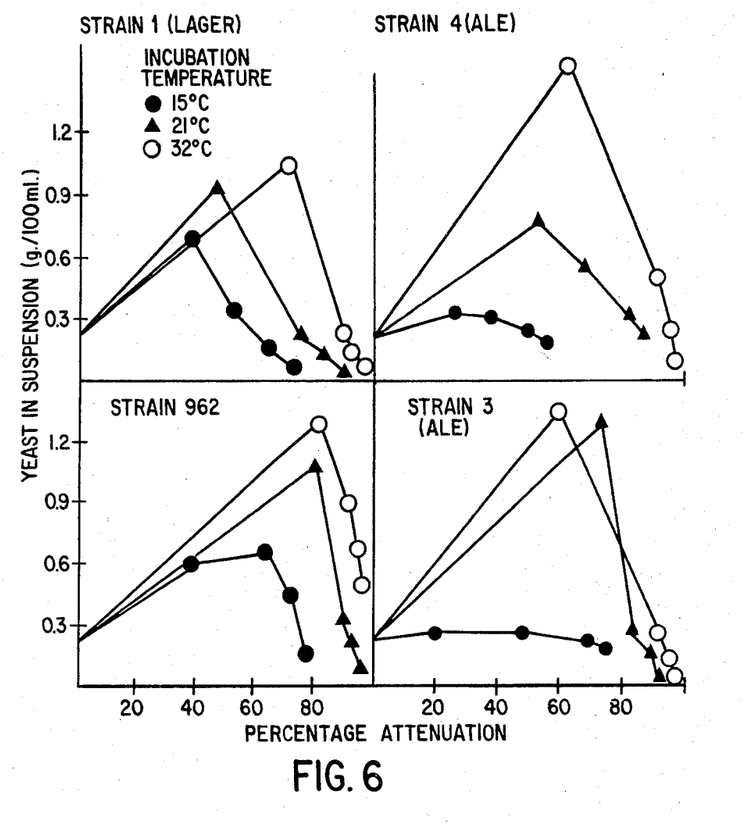
FIG. 6 is a collection of graphs showing the effect of growth temperature on the flocculation characteristics of a number of brewers' yeast strains, including the novel strain of the invention, during static culture in a 12°P wort.

It has also been well documented in the literature that the incubation or growth temperature during the growth of certain yeast strains will influence the strains' flocculation characteristics. In order to determine this influence of incubation temperature, a number of ale and lager yeast strains were cultured in wort of the type and in the manner defined above and the fermentation and flocculation characteristics were again examined in a 20 liter static fermenter with 12° P wort at about 15° C., 21° C. and 32° C. The results are shown graphically in FIG. 6 wherein, as before, the yeast in suspension is plotted against percentage attenuation of the wort.

From this series of experiments it was noted that neither ale strain 3 or 4 grew to any significant extent when cultured at about 15° C. and as a result (see FIG. 6) comparatively little yeast in suspension accumulated. At the end of the fermentation period both of these strains attenuated the wort to about 60% to 75% of its potential attenuation. At the higher temperatures of about 21° C. and 32° C. ale strains 3 and 4 exhibited greater growth and delayed flocculence with increased temperature. In contrast, the lager strain 1 grew well at 15° C. With an increase in temperature, this lager strain also exhibited an increased ability to multiply and delay its flocculation. It is obvious from FIG. 6 that lager strain 1 was much less affected by incubation temperature than ale strains 3 and 4.

The effect of temperature on yeast flocculation would appear to be strain dependent and as in many other situations each strain must be considered as a separate entity although generalization between groups of species or strains, such as lager and ale, can be made. As a result of this study it is possible to note that while most strains of *Saccharomyces cerevisiae* fail to grow well below about 20° C. when compared to strains of *Saccharomyces uvarum* (*carlsbergensis*), the bottom-cropping ale strain 962 which taxonomically is classified as *Saccharomyces cerevisiae*, exhibits an ability to grow well at about 15° C. and 32° C. which is a trait generally more indicative of lager strains than ale strains. These results agree generally with reports in the literature which show that strains of *Saccharomyces uvarum* (*carlsbergensis*) grow well over the range of about 8° C. to 30° C. but not above about 36° C. whereas strains of *Saccharomyces cerevisiae* have a maximum growth temperature of about 44° C. with poor growth below about 18° C.

(c) Effect of Pitching Rate on Flocculation

Figure 7:
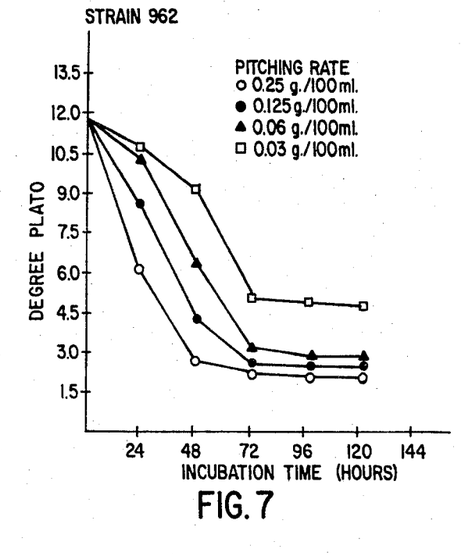
FIG. 7 is a graph showing the effect of the pitching rate on the fermentation characteristics of the novel yeast strain of the present invention under static fermentation conditions in an 11.8°P wort.
Figure 8:
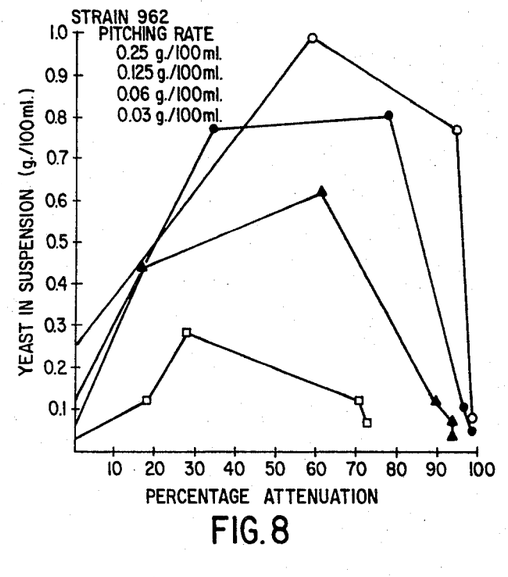
FIG. 8 is a graph showing the effect of the pitching rate on the flocculation characteristics of the novel yeast strain of this invention under static fermentation conditions in an 11.8°P wort.

The effect of the yeast pitching rate on fermentation and flocculation in static fermentation was studied with a number of ale strains and since the results generally were similar, only those obtained using strain 962 will be discussed and considered representative (see FIGS. 7 and 8). From FIG. 7 it may be seen that reduction of the pitching rate from about 0.25% to 0.125% (w/v) wet weight in an 11.8°P wort containing about 30% corn adjunct had the effect of producing a slight initial lag phase but following approximately 72 hours fermentation the two fermentations exhibited quite similar characteristics and both attenuated the wort well with very little yeast left in suspension. This initial lag phase became increasingly pronounced as the pitching rate was decreased. Not only was the initial lag phase more pronounced at pitching rates of about 0.06% and 0.03% (w/v), but there was a concurrent substantial reduction in the total yeast growth as seen most readily in FIG. 8. It is also noteworthy that, again as seen in FIG. 8, a decrease in pitching rate resulted generally in premature flocculation which in turn resulted in incomplete attenuation of the wort.

III. The present invention will be further described with reference to the following examples detailing the preparation of ale using the subject yeast strain and standard brewhouse equipment and procedures familiar to those skilled in the art of brewing.

EXAMPLE 1

A corn grit adjunct was prepared in a cereal cooker by heating the corn grits in water at about 71° C. for about 10 minutes. The adjunct material was then brought to boil and introduced into the mash mixer and combined with regular brewing malt which had been heated in water at a temperature of about 48° C. for about 20 minutes in proportions sufficient to achieve a wort having about 30% corn adjunct. The mixture so formed was heated heated at about 67° C. for about 30 minutes and thereafter at approximately 77° C. for about 5 minutes. Using standard lautering procedures, about 529 hectoliters of wort were obtained and introduced into the kettle where hops were added and the kettle contents boiled for about one hour. The hops, as well as other trub components such as proteinaceous matter, were then separated from the wort which was cooled, oxygenated and pumped to a fermenter to achieve about 1460 hectoliters of approximately 16.4°P and having a temperature of about 17° C. Yeast strain 962 was added in an amount of about 400 gram/hectoliter and the heat generated by the respiration of the yeast was used to increase the temperature to about 21° C., termed "free-rise" in the art. The fermentation was allowed to proceed at a constant temperature of about 21° C., maintained by cooling, for a period of about 48 hours. The attenuated wort so obtained exhibited a plato value of about 2.9°P. Thereafter, the fermenter contents were cooled and treated utilizing standard brewing procedures and techniques to finish the ale. Dissolved oxygen-free water was introduced into the ale after final filtration to reduce the alcohol content from about 6.8% by volume to 4.85% by volume.

Analysis of the resulting finished beer provided the following data:

| | |
|---|---|
| Air (ml) | 0.6 |
| $CO_2$ (vol.) | 2.72 |
| Colour (°SRM) | 3.9 |
| Foam (sec.) | 130.0 |
| Apparent Extract (%) | 2.5 |
| Real Extract (%) | 4.22 |
| Calculated Original Extract (%) | 11.6 |
| Alcohol (% vol.) | 4.85 |
| Yeast Ferm. Ext. (%) | 0.3 |
| pH | 4.2 |
| Copper (ppm) | 0.07 |
| Bitterness Units | 18.5 |
| Forced Haze Test (FTU) (1 week) | 180.0 |

The above analysis and those of the succeeding examples were effected in accordance with the procedures published by the American Society of Brewing Chemists in "Methods of Analysis of the American Society of Brewing Chemists", seventh revised edition, 1976.

Representative samples of the finished beer were evaluated by taste test panels employing the Triangular Test, which is a standard statistical test in the brewing art used to determine the difference, if any, of the organoleptic properties of selected products. The organoleptic characteristics analyzed by taste test panelists include the following:

| Aroma | | |
|---|---|---|
| | hop | ester |
| | yeast | freshness |
| Taste | | |
| | fullness | yeast |
| | sweetness | ester |
| | bitterness | freshness |
| | after bitter | metallic |
| | acid | smoothness |

Of the above attributes, taste test panelists reported a significantly higher (at the 95% confidence limit) ester aroma and taste in the ale produced by yeast strain 962 compared with the presently most popular commercially produced Canadian ale. All other attributes were statistically similar. The higher ester content imparted a slightly sweeter taste to the ale produced by the subject yeast strain.

The taste test analysis makes evident that the ale produced by the yeast strain of this invention is qualitatively commercially acceptable by present standards.

EXAMPLE 2

Using the procedure detailed in Example 1 above, approximately 1460 hectoliters of a hopped, about 30% corn grit adjunct wort having a plato value of about 14.0°P were prepared and introduced into a fermenter, whereafter 300 gram/hectoliter of yeast strain 962 was added to effect the "free-rise" and fermentation. The wort was fermented for about 72 hours at about 21° C.

to about 2.4°P. The fermenter contents were then cooled and treated using standard brewing procedures and techniques. Following the final filtration, oxygen-free water was included in the beer to reduce the alcohol content from about 5.8% by volume to 4.82% by volume.

The ale so obtained was analyzed and found to have the following properties:

| | |
|---|---|
| Air (ml) | 0.4 |
| $CO_2$ (vol.) | 2.86 |
| Colour ("SRM) | 3.9 |
| Foam (sec.) | 124.0 |
| Apparent Extract (%) | 2.0 |
| Real Extract (%) | 3.81 |
| Calculated Original Extract (%) | 11.2 |
| pH | 4.2 |
| Copper (ppm) | 0.2 |
| Bitterness Units | 15.5 |
| Alcohol (% vol.) | 4.82 |
| Forced Haze Test (FTU) (1 week) | 120.0 |

Evaluation of this ale by a taste test panel, as detailed in Example 1, showed there was no significant difference between it and the presently most popular commercial Canadian ale.

EXAMPLE 3

By the process described in Example 1, about 490 hectoliters of a 12.0°P, hopped, about 30% corn grit adjunct wort were prepared. Following introduction of the wort into the fermenter, yeast strain 962 was added in an amount of 300 gram/hectoliter. The temperature was raised to about 21° C. by "free-rise" and the fermentation of the wort was then carried out at about 21° C. The wort was fermented for about 72 hours to about 2.2°P. Thereafter, the fermenter contents were cooled and processed by standard brewing procedures and techniques to produce a finished ale having an alcohol content of 5.10% by volume.

Analysis of the ale so produced provided the following data:

| | |
|---|---|
| Air (ml) | 1.0 |
| $CO_2$ (vol.) | 2.63 |
| Colour ("SRM) | 3.5 |
| Foam (sec.) | 121.0 |
| Apparent Extract (%) | 2.0 |
| Real Extract (%) | 3.92 |
| Calculated Original Extract (%) | 11.7 |
| pH | 4.05 |
| Copper (ppm) | 0.12 |
| Bitterness Units | 14.0 |
| Alcohol (% vol.) | 5.10 |
| Forced Haze Test (FTU) (1 week) | 180.0 |

Taste test data, obtained by the test described in Example 1, showed that the ale so produced was not significantly different overall from the presently most popular commercial Canadian ale.

The data derived from this and the previous examples show that ale products produced by yeast strain 962 from high gravity worts and from regular gravity worts are of consistent quality.

What we claim is:

1. In a brewing process wherein a malt wort is prepared; fermented with brewers' yeast; and, following completion of the fermentation, finished to the desired alcoholic brewery beverage; the improvement comprising fermenting said wort having a Plato value of about 14.5 or greater with a strain of the species *Saccharomyces cerevisiae* brewers' yeast having the NCYC No. 962.

2. In a process as claimed in claim 1, wherein the wort to be fermented has a Plato value of up to about 18°P.

3. In a process as claimed in claim 1, wherein the said yeast is added to said wort in an amount of from 0.125 to 0.25 gm/100 ml.

4. In a process as claimed in claim 2, wherein the said yeast is added to said wort in an amount of from 0.125 to 0.25 gm/100 ml.

5. In a process as claimed in claim 1, 2 or 3, wherein the fermentation temperature is about 21° C.

6. In a brewing process for producing ale, wherein a hopped, 30% corn grit adjunct wort is prepared having a Plato value of from about 16°P to 18°P; fermented at a temperature of about 21° C. for about 3 to 5 days with a species of *Saccharomyces cerevisiae* brewers' yeast; and, following completion of the fermentation, finished to the desired ale; the improvement comprising fermenting said wort with a strain of the species *Saccharomyces cerevisiae* brewers' yeast having the NCYC No. 962.

7. A biologically pure culture of a brewer's yeast strain of the species *Saccharomyces cerevisiae* having the NCYC No. 962, said strain having the ability to ferment high Plato value worts of 14.5 or greater and the ability of flocculate to the bottom of the fermentation vessel when attenuation is substantially complete.

8. In a method of manufacturing a novel brewers' yeast strain, wherein a yeast strain is propagated in an oxygenated nutrient medium, the improvement comprising propagating a biologically pure culture of a yeast strain of the species *Saccharomyces cerevisiae* having the NCYC No. 962.

9. A biologically pure culture of a brewer's yeast strain of species *Saccharomyces cerevisiae* having the NCYC No. 962, whenever prepared by the process as claimed in claim 8, said strain having the ability to ferment high Plato value worts of 14.5 or greater and the ability to flocculate to the bottom of the fermentation vessel when attenuation is substantially complete.

* * * * *